(12) United States Patent
Kiguchi et al.

(10) Patent No.: US 9,339,191 B2
(45) Date of Patent: May 17, 2016

(54) OPTICAL MEASUREMENT APPARATUS

(75) Inventors: Masashi Kiguchi, Kawagoe (JP);
Tsukasa Funane, Fujimi (JP); Kei Utsugi, Tokyo (JP); Atsushi Suzuki, Higashiyamato (JP)

(73) Assignee: Hitachi, Ltd., Tokyo (JP)

( * ) Notice: Subject to any disclaimer, the term of this patent is extended or adjusted under 35 U.S.C. 154(b) by 351 days.

(21) Appl. No.: 13/002,411

(22) PCT Filed: Jun. 15, 2009

(86) PCT No.: PCT/JP2009/060876
§ 371 (c)(1),
(2), (4) Date: Jan. 18, 2011

(87) PCT Pub. No.: WO2010/004835
PCT Pub. Date: Jan. 14, 2010

(65) Prior Publication Data
US 2011/0260065 A1    Oct. 27, 2011

(30) Foreign Application Priority Data
Jul. 8, 2008    (JP) ................. 2008-177483

(51) Int. Cl.
*F21V 9/16*    (2006.01)
*A61B 5/00*    (2006.01)
(Continued)

(52) U.S. Cl.
CPC ........... *A61B 5/0059* (2013.01); *A61B 5/02028* (2013.01); *A61B 5/0261* (2013.01);
(Continued)

(58) Field of Classification Search
CPC ...... G01T 1/20; G01K 11/20; G01N 21/6428; G01N 33/582; G01N 21/6458; G01N 21/645; G01N 2201/3144; G01N 21/359; G01N 21/4795; H01L 27/144; A61B 5/0059; A61B 5/0261; A61B 5/02028
USPC .............. 250/458.1, 261, 461.1–461.2, 459.1
See application file for complete search history.

(56) References Cited

U.S. PATENT DOCUMENTS 2,687,360 A * 8/1954 Michaels ............... C09K 11/02
250/486.1
4,215,275 A * 7/1980 Wickersheim ............ G01J 5/48
356/44

(Continued)

FOREIGN PATENT DOCUMENTS

CN    1100619    3/1995
CN    1882276    12/2006
(Continued)

OTHER PUBLICATIONS

Author: Jean-Luc Lemyre and Anna M. Ritcey, Title: Synthesis of Lanthanide Fluoride Nanoparticles of Varying Shape and Size, Date: Aug. 29-Sep. 2, 2005, Publisher: TNT2005, Oviedo-Spain.*

(Continued)

*Primary Examiner* — David J Makiya
*Assistant Examiner* — Taeho Jo
(74) *Attorney, Agent, or Firm* — Mattingly & Malur, PC

(57) ABSTRACT

Provided is a near-infrared spectroscopy apparatus using a phosphor. [Object]: Information in a specimen is observed by using light without contacting an optical fiber and an electronic circuit with the specimen. [Means for Solution]: A small and lightweight phosphor is contacted with the specimen to measure the fluorescence intensity at a separate position.

7 Claims, 5 Drawing Sheets

(51) Int. Cl.
*A61B 5/02* (2006.01)
*A61B 5/026* (2006.01)
*G01N 21/47* (2006.01)
*G01N 21/64* (2006.01)
*G01N 21/359* (2014.01)
*G01N 21/31* (2006.01)

(52) U.S. Cl.
CPC .......... *G01N21/4795* (2013.01); *G01N 21/645* (2013.01); *G01N 21/359* (2013.01); *G01N 2021/3144* (2013.01)

(56) References Cited

U.S. PATENT DOCUMENTS

| | | | | |
|---|---|---|---|---|
| 4,901,238 | A | | 2/1990 | Suzuki et al. |
| 5,200,838 | A | * | 4/1993 | Nudelman ............ A61B 1/0008 257/E31.115 |
| 5,304,809 | A | * | 4/1994 | Wickersheim ..... G01N 21/6408 250/458.1 |
| 5,459,323 | A | * | 10/1995 | Morgan .............. G01N 21/6408 250/458.1 |
| 5,593,899 | A | * | 1/1997 | Wilson ................. A61B 5/0059 422/79 |
| 5,760,406 | A | * | 6/1998 | Powers .................... C12Q 1/04 250/459.1 |
| 5,784,162 | A | * | 7/1998 | Cabib .................. C12Q 1/6841 250/461.2 |
| 6,123,455 | A | * | 9/2000 | Beshears ................ G01K 11/20 374/159 |
| 6,399,397 | B1 | * | 6/2002 | Zarling .................. B82Y 15/00 435/7.1 |
| 6,615,063 | B1 | | 9/2003 | Ntziachristos et al. |
| 7,283,229 | B2 | * | 10/2007 | Noguchi et al. ............. 356/317 |
| 7,328,059 | B2 | * | 2/2008 | Sevick-Muraca .... A61B 5/0059 600/431 |
| 7,599,731 | B2 | * | 10/2009 | Rice et al. ...................... 600/473 |
| 7,983,740 | B2 | * | 7/2011 | Culver ................. A61B 5/0073 600/473 |
| 8,174,686 | B2 | * | 5/2012 | Namba et al. .................... 356/123 |
| 8,190,231 | B2 | | 5/2012 | Miwa et al. |
| 2002/0150944 | A1 | * | 10/2002 | Hosoi ................... B01L 3/5085 506/7 |
| 2002/0155589 | A1 | * | 10/2002 | Tsuchiya .......... G01N 33/54393 435/287.2 |
| 2003/0205681 | A1 | * | 11/2003 | Modlin .............. G01N 21/6428 250/458.1 |
| 2004/0015062 | A1 | | 1/2004 | Ntziachristos et al. |
| 2004/0095568 | A1 | * | 5/2004 | Noguchi ............ G01N 15/1456 356/73 |
| 2006/0103291 | A1 | * | 5/2006 | Ellens et al. ................... 313/485 |
| 2006/0197034 | A1 | * | 9/2006 | Shirai ................ G01N 21/6428 250/458.1 |
| 2006/0266958 | A1 | * | 11/2006 | Shimizu ................ G01N 21/253 250/583 |
| 2007/0253908 | A1 | * | 11/2007 | Rice ..................... A61B 5/0073 424/9.4 |
| 2008/0219933 | A1 | | 9/2008 | Ntziachristos et al. |
| 2008/0225278 | A1 | * | 9/2008 | Namba .............. G01N 21/6458 356/123 |
| 2009/0220415 | A1 | | 9/2009 | Shachaf et al. |
| 2010/0030084 | A1 | * | 2/2010 | Ziegler ................. A61B 5/0091 600/476 |

FOREIGN PATENT DOCUMENTS

| | | |
|---|---|---|
| JP | 63-275323 A | 11/1988 |
| JP | 9-140715 A | 6/1997 |
| JP | 2003-339677 A | 12/2003 |
| JP | 2006-102110 A | 4/2006 |
| JP | 2007-82769 A | 4/2007 |
| JP | 2008-149154 A | 7/2008 |
| WO | 2007075565 | 7/2007 |
| WO | WO 2007075565 A2 * | 7/2007 |
| WO | 2008059434 | 5/2008 |

OTHER PUBLICATIONS

Author: Lemyre and Anna M. Ritcey, Title: Synthesis of Lanthanide Fluoride Nanoparticles of Varying Shape and Size, Date:Apr. 29, 2005, Publisher: American Chemical Society.*
CN Office Action in CN Application No. 200980125008.8, dated Jul. 20, 2012.
EP Supplementary Search Report in EP App. No. 09794282.5, dated Mar. 12, 2013.
Communication pursuant to Article 94(3) EPC received in corresponding European Application No. 09794282.5 dated Jun. 3, 2015.

* cited by examiner

FORMULA 1

$$(Nd_{0.9}Yb_{0.1})_2O_3 : Li_2O : P_2O_5$$

OPTICAL MEASUREMENT APPARATUS

TECHNICAL FIELD

The present invention relates to an apparatus which irradiates a specimen to be examined (hereinafter, simply referred to as specimen) with light to measure internal information of the specimen in a noninvasive manner.

BACKGROUND ART

The absorption spectroscopy in which a specimen is irradiated with light in a wavelength range from ultraviolet to near-infrared and the amount of transmitted light is measured to determine the characteristics of the specimen has been widely known. In general, when performing the absorption spectroscopy, the distance passed through the specimen and the light amount attenuated after passing through the specimen are measured. When it is difficult to measure the transmitted light due to the strong absorption and scattering of the specimen, the reflection configuration is used, that is, a detector is disposed on the same side as a light source against the specimen. When the scattering of the specimen is strong, a position irradiated with light on a surface of the specimen is made different from a position at which the light is detected on the surface of the specimen, whereby the light passed through the inside of the specimen can be detected and the information inside the specimen can be obtained.

In particular, when the specimen is a living thing, the scattering is strong and an optical system with the reflection configuration is used in many cases. The technology of measuring or observing the hemodynamic in a living tissue in a noninvasive manner by using a method of absorption spectroscopy has been widely known, and an apparatus which measures the oxygen metabolism state in a tissue and observes a brain activity state by measuring the hemodynamic of a brain has been realized and applied to the medical and industrial fields. This apparatus is described in, for example, Japanese Patent Application Laid-Open Publication No. 57-115232 (Patent Document 1), Japanese Patent Application Laid-Open Publication No. 63-260532 (Patent Document 2), Japanese Patent Application Laid-Open Publication No. 63-275323 (Patent Document 3), Japanese Patent Application Laid-Open Publication No. 9-140715 (Patent Document 4) and Japanese Patent Application Laid-Open Publication No. 2003-339677 (Patent Document 5).

PRIOR ART DOCUMENT

Patent Document

Patent Document 1: Japanese Patent Application Laid-Open Publication No. 57-115232
Patent Document 2: Japanese Patent Application Laid-Open Publication No. 63-260532
Patent Document 3: Japanese Patent Application Laid-Open Publication No. 63-275323
Patent Document 4: Japanese Patent Application Laid-Open Publication No. 9-140715
Patent Document 5: Japanese Patent Application Laid-Open Publication No. 2003-339677

SUMMARY OF THE INVENTION

Problems to be Solved by the Invention

When an intensity of light ejected from a position different from the incident position of the light is measured, the spatial filtering is usually provided by using a lens and small pores. When a specimen is a scattering body such as a living thing, since the detection light is incoherent and the intensity of the light which is ejected from a position other than the position where the light is supposed to be detected (hereinafter, referred to as detection position) is high, it is difficult to separately detect only the light from the detection position by the spatial filter. Therefore, the spatial filtering has been conventionally performed by directly contacting an optical fiber or an optical detector with the detection position on a surface of the specimen. For example, FIG. 1 shows a typical configuration diagram thereof. Here, the reference number 11 denotes an irradiation optical fiber, 12 denotes a detection optical fiber, and 13 denotes a specimen. In this case, there are a problem that the optical fiber cannot be contacted well depending on the shape of the specimen surface and a problem that a motion and a posture of the specimen are restricted in come cases by large components such as the contacted fiber and circuit.

An object of the present invention is to provide an apparatus having a mechanism capable of detecting an intensity of light ejected from a detection position separately from light ejected from other positions without directly contacting a fiber and an optical detector with a surface of a specimen even when the specimen has strong scattering.

Means for Solving the Problems

An optical measurement apparatus of the present invention includes: one or plural mechanisms which make light incident into a specimen; one or plural luminescent materials which are disposed at a position (detection position) apart from an incident position of the specimen and are excited by light with a wavelength of the incident light; and one or plural mechanisms which detect light emitted from the luminescent material. Since the light emitted from the luminescent material is different in wavelength from the incident light, the intensity thereof can be measured separately from the incident light by using a wavelength separation method such as an optical filter. Since a luminescence intensity is proportional to an intensity of light with which the luminescent material is irradiated at the detection position, the intensity of the light which is incident from the incident position, passes through the specimen and is then ejected from the detection position can be obtained by measuring the luminescence intensity.

When the luminescent materials are disposed at plural detection positions, light distribution on the surface of the specimen can be measured. The following is the methods of separately observing the respective detection positions. That is, an optical waveguide such as an optical fiber is contacted with or disposed near each of the luminescent materials to prevent the entrance of lights from other luminescent materials. Lights from each of the luminescent materials are separated by using an imaging system. Luminescent materials having different luminescence wavelengths are used and lights from each of the luminescent materials are separated by using a wavelength separation method such as an optical filter.

At this time, in order to prevent the light emission of the luminescent materials, which occurs when light ejected from a position other than the detection position and light scattered on the surface are shed to the luminescent materials, surfaces of the luminescent materials other than the surface in contact with the specimen may be covered with a member which shields the incident light wavelength. However, in order to measure the luminescence intensity from the luminescent material, at least a part of the shielding member has to transmit the luminescence wavelength.

When the positional relation between the luminescent material and the optical detector is changed, the detection efficiency is changed depending on an angle of view of the optical detector with respect to an emission pattern of the emitted light, and the detection light intensity is changed. Since the luminescent material can be captured as an image when an image-pickup tube is used as the optical detector, the positional relation between the optical detector and the luminescent material can be obtained from the size and shape of the image. In other words, the detection efficiency can be adjusted and corrected by using the size and shape of the image. The method of calculating the positional relation from the shape of the image has been publicly known, and this can be easily and accurately performed when the image is a triangle. Therefore, the luminescent material is preferably formed to have a triangular shape.

The optical system can irradiate the incident position of the specimen with the incident light in a noncontact manner. In order to clearly show the incident position, a marker may be disposed at a target incident position of the specimen. Furthermore, by using a tracking mechanism, the light irradiation to the same incident position can be maintained even when the specimen moves. At this time, the incident light intensity differs depending on the incident angle of the light. Since the distance and the angle with respect to the specimen are measured at the time of tracking, the relation between these parameters and the incident light intensity to the specimen is corrected in advance to adjust the detection light intensity.

Hereinafter, in this specification, a head of a living thing is taken as an example of the specimen, and the configuration in which the optical detector and the light source are disposed on the same side with respect to the specimen, that is, an example of the reflection configuration will be described. However, the present invention can be applied in the same manner even when the specimen is a part of a living thing other than a head or is not a living thing, and the present invention can be applied to any configuration regardless of the positions of the optical detector, the light source and the specimen.

Effects of the Invention

When the present invention is used, only by disposing a small marker and a luminescent material on a specimen, the optical absorption information in the specimen can be measured. Therefore, the simple measurement with less restriction on the specimen can be achieved. Furthermore, when the specimen is a living thing, the effect that the comfort of the subject can be increased can be achieved.

BRIEF DESCRIPTIONS OF THE DRAWINGS

BEST MODE FOR CARRYING OUT THE INVENTION

First Embodiment

Figure 1:
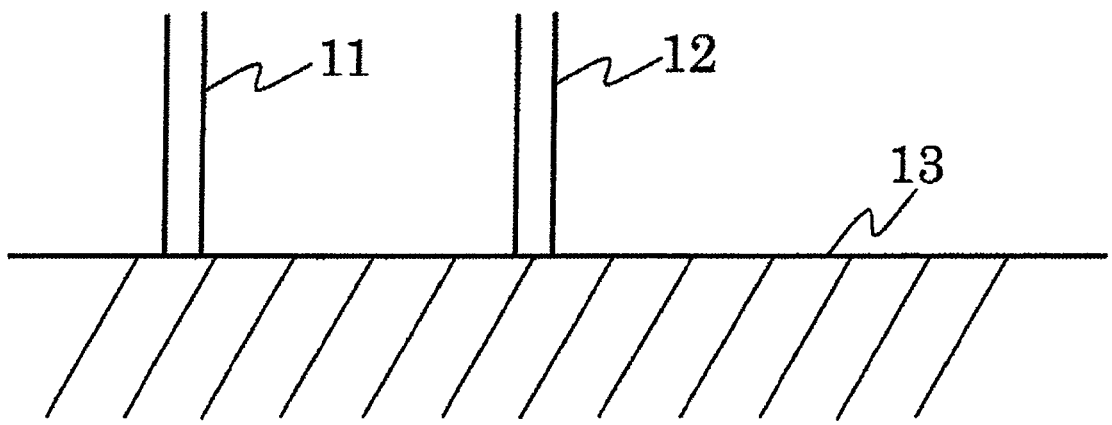
FIG. 1 is a diagram for describing a conventional measurement configuration.
Figure 2:
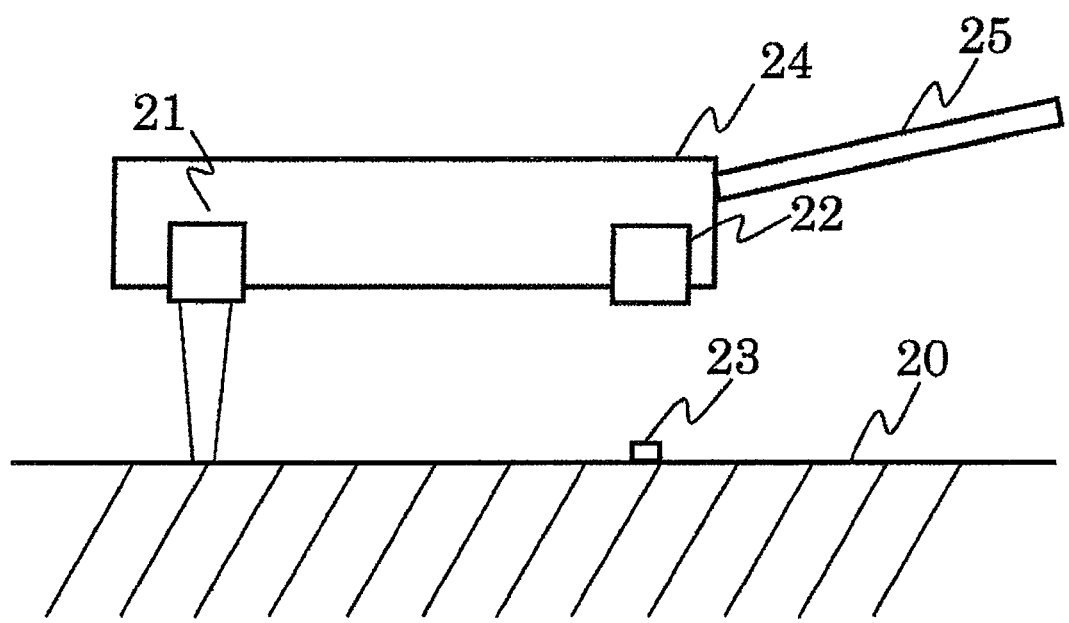
FIG. 2 is a diagram showing an example of a measurement configuration.

An embodiment of the present invention will be described with reference to FIG. 2. A semiconductor laser 21 with a wavelength of 830 nm and an optical detector 22 are fixed to a chassis 24 so as to be spaced apart by a distance of 30 mm. A phosphor cell 23 is fixed onto a forehead scalp 20 with paste. The semiconductor laser 21 irradiates a position on the forehead scalp apart from the phosphor cell 23 by 30 mm with the output light thereof. Although omitted in FIG. 2, the optical detector 22 uses an avalanche photodiode as an optical detection element, and an InP crystal is disposed as an optical filter, which transmits fluorescence emitted from the phosphor 23 but does not transmit irradiated light, in front of a light acceptance surface of the optical detector 22. Furthermore, a lens optical system for efficiently receiving the light from the phosphor cell 23 is also provided. The chassis has an arm 25 capable of being fixed to a part of head or body or another apparatus.

Figures 7, 8:
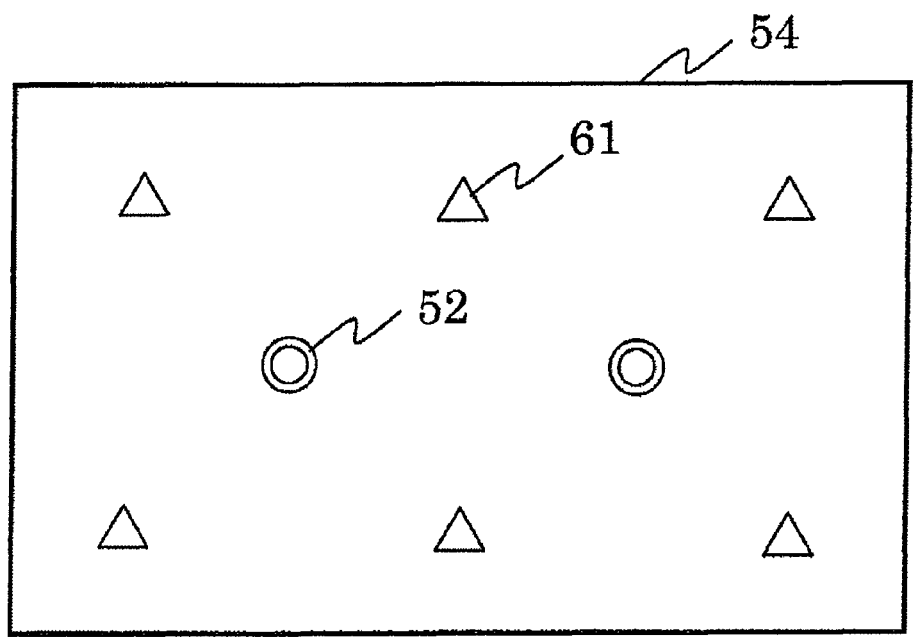
FIG. 7 is a diagram showing an example of a specimen applied portion.
FIG. 8 shows the contents of the formula 1.

For example, the phosphor used here is a compound expressed by the formula 1 shown in FIG. 8 and emits fluorescence with the wavelength of about 1 μm when excited by the wavelength of 0.8 μm. Since the excitation light has a wavelength which is relatively high in permeability to a living thing, the phosphor 23 is excited by the light which is incident into the head from the position irradiated by the semiconductor laser 21 and returns through cerebral cortex. Since the fluorescence intensity is proportional to the excitation light intensity, the change of absorption in the cerebral cortex can be observed by measuring the fluorescence intensity by the optical detector. Although the case of a light source of one wavelength has been described here for simplification, the blood volume and the oxygenation state can be also observed by using a light source of two or more wavelengths like in a usual case.

The phosphor used here is suitable for the measurement of the hemodynamic in a living thing because it can be excited by near-infrared light with a wavelength of about 0.8 μm. In other cases, any material can be used as long as it is excited by a wavelength used to obtain the absorption information in a living thing and emits light, and phosphorescence, Raman scattered light and others can also be used other than fluorescence.

Figure 3:
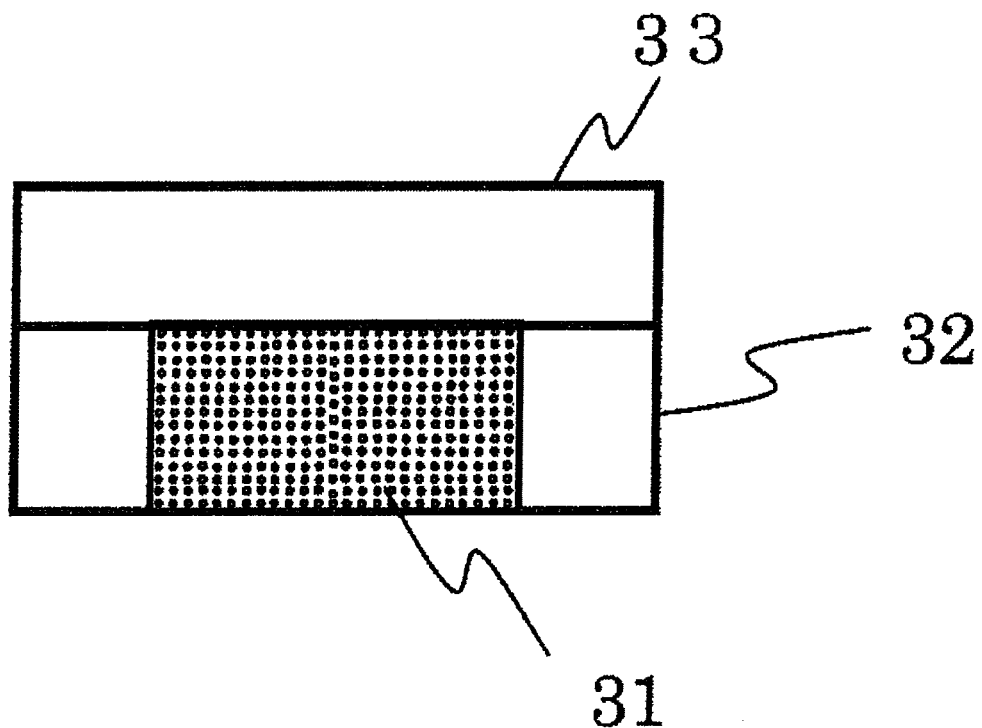
FIG. 3 is a diagram showing an example of a phosphor cell.

FIG. 3 is a cross-sectional view of the phosphor cell 23. Phosphor powder 31 is distributed in resin filled in a metal 32, and a filter 33 made of InP is put as a lid thereon. A filter having the characteristics of not transmitting the excitation light, that is, the irradiated light and transmitting fluorescence is used as the filter 33. The metal 32 may be made of resin or the like as long as it does not transmit the irradiated light. By using the phosphor cell 23 while bringing a surface opposite to the filter 33 into contact with the specimen, the excitation of the phosphor by the stray light other than the light transmitted through the inside of the specimen can be prevented.

Second Embodiment

Figure 4:
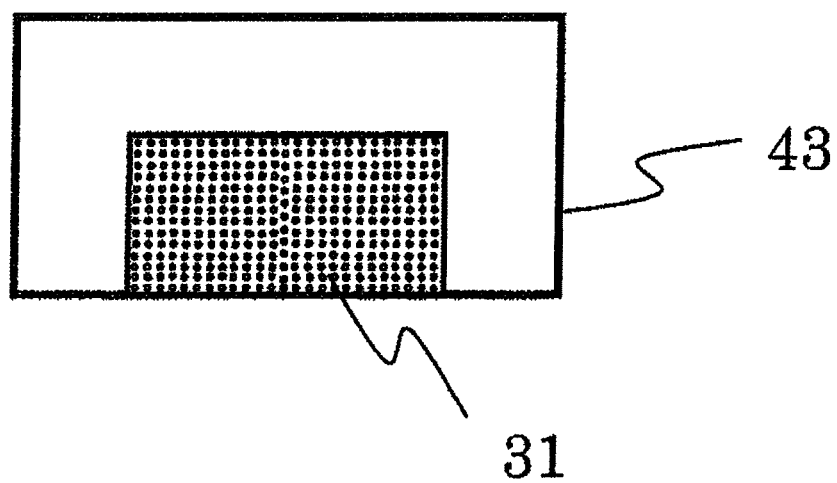
FIG. 4 is a diagram showing an example of an integral-type phosphor cell.

FIG. 4 shows another embodiment of the phosphor cell described in the first embodiment. While the metal and the lid are fabricated from different materials in FIG. 3, a filter 43 made of InP is processed and integrally formed as a single piece in FIG. 4. The effect of cost reduction compared with the phosphor cell of the first embodiment can be achieved.

Third Embodiment

Figure 5:
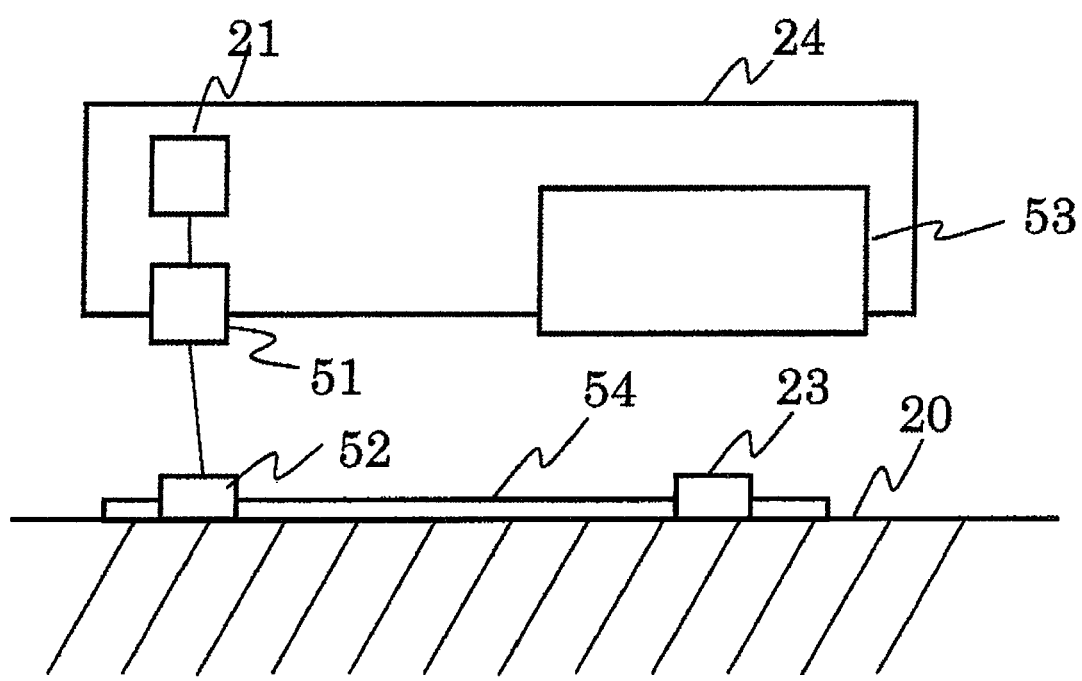
FIG. 5 is a diagram showing another example of a measurement configuration.

Another embodiment of the present invention will be described with reference to FIG. 5. A marker 52 and the phosphor cell 23 are fixed to a sheet 54, and the sheet 54 is contacted and fixed onto the forehead scalp 20. Here, the marker 52 and the phosphor cell 23 can be separately attached to the specimen, but the distance therebetween can be easily determined when the sheet 54 is used. The marker 52 is irradiated with the light ejected from the semiconductor laser 21 by a beam tracking device 51. The marker 52 is made of a material whose scattering and absorption with respect to the wavelength of the irradiated light are small. Alternatively, the marker 52 may be formed into a toroidal shape to irradiate a central hole with the light. The fluorescence from the phosphor is observed as an image by an image-pickup tube 53.

In this configuration, by measuring the size and shape of the phosphor cell, the angle of view and the distance thereof can be calculated. Since the detection efficiency of the fluorescence differs depending on the angle of view and the distance, the fluorescence intensity is corrected based on these calculation results. Similarly, since the intensity and incident position of the light incident into the specimen are changed also on the irradiation side when the incident angle and the distance are changed, the detection fluorescence intensity is corrected by using the angle of view and the distance obtained in the tracking. By this means, the effect that it becomes unnecessary to strictly adjust the positional relation between the irradiation-detection system and the specimen and the measurement is facilitated can be achieved. Furthermore, since the correction of the fluorescence intensity will be all that is needed even when the specimen moves, the effect that the application to a specimen that is difficult to fix such as a living thing is possible is also achieved. The chassis 24 is used as being held by the arm near the head in the same manner as the first embodiment, but it may have a structure of taking images while being held by the human hand.

Here, means of correcting the fluorescence intensity based on the angle of view and the distance will be described. The phosphor cell is excited by a predetermined light intensity to emit light in advance. By using the optical detector, the angle of viewing the phosphor cell and the distance to the phosphor cell are changed and the detected fluorescence intensity is measured. Furthermore, the normalization is performed by dividing the detected fluorescence light intensity by the irradiated light intensity to obtain the light detection efficiency. Alternatively, the normalization may be performed by the division using one angle and distance, for example, the values when an optical detector is contacted with a phosphor cell. By this means, the table of the relative values of the optical detection efficiency using the distance and angle as parameters can be obtained. In the actual measurement, the values of the distance and angle to the phosphor cell are calculated from an image of the size and shape of the phosphor cell, and the table is interpolated by using the values to calculate the optical detection efficiency and perform a multiplication with using it as a correction factor.

Also on the irradiation side, the correction can be made by using the distance and angle from the irradiation light source to the marker. Although the distance and angle obtained in the tracking are used for the correction here, they may be obtained from an image by using a triangular marker. In this case, an image-pickup tube for the fluorescence measurement can also be used. An optical filter which transmits the fluorescence wavelength and shields the irradiated light and the background light is provided in order to enhance the detection sensitivity of the fluorescence. In this case, since the marker shape cannot be obtained as an image, it is preferable to temporarily illuminate the marker for the shape observation by using the light transmitted through the optical filter. Alternatively, another image-pickup tube having no optical filter may be used separately from the image-pickup tube for the fluorescence measurement.

Fourth Embodiment

Figure 6:
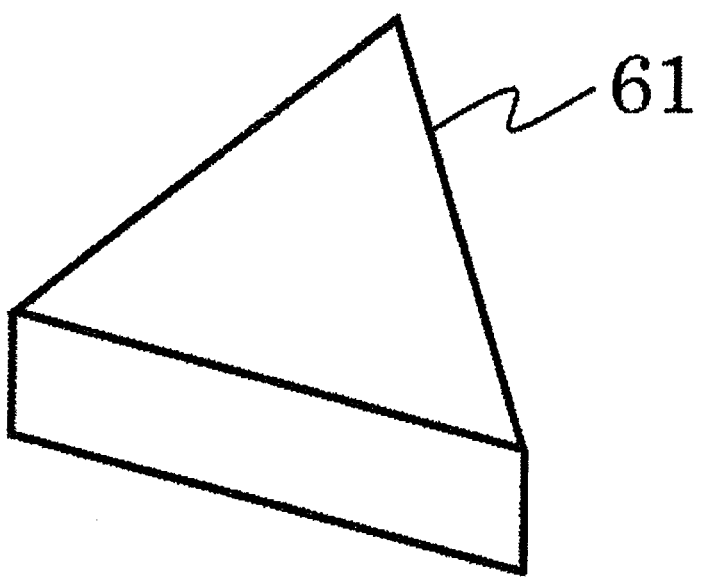
FIG. 6 is a diagram showing an example of a triangular phosphor cell.

FIG. 6 shows an example of the phosphor cell used in the fourth embodiment. Since the phosphor cell is designed to have a general shape of a triangular prism, the distance and angle of view to the phosphor cell can be easily processed by software based on the angle between the sides of the triangle and the slope and length of the sides of the triangle.

Fifth Embodiment

FIG. 7 shows an example in which the markers 52 and phosphor cells 61 are disposed on a lattice sheet 54. This is applied to a specimen. Since the components are small and lightweight, it is possible to have flexibility enough to be attached along the shape of the specimen. Furthermore, it is also possible to easily wear it on the head or wear it on the arm or leg by forming it to have a shape of a hat or a browband.

A plurality of phosphor cells are separated by image formation. Also, since fluorescences with different wavelengths are generated from each cell when different fluorescence materials are provided for each of the phosphor cells, the phosphor cells may be separated by the fluorescence wavelength by using the optical filter and the like.

INDUSTRIAL APPLICABILITY

A brain function measuring apparatus using near-infrared spectroscopy can be used as medical and research equipment or for the confirmation of the educational effect, the health management at home, the market research of a product monitoring and others. Further, it can also be used for the measurement of the tissue oxygen saturation and the measurement of the muscle oxygen metabolism. Furthermore, it can also be used for the usual absorption spectroscopy apparatus, including the measurement of the sugar content of a fruit.

The invention claimed is:

1. An optical measurement apparatus comprising:
one or more light irradiators, each of which irradiates light with a wavelength of 200 nm to 1500 nm onto a living object at an incident light position on a surface of the living object, respectively;
one or more luminescent cells, each of which is filled with a luminescent material and has a first surface which is disposed directly on the surface of the living object at a light detection position spaced apart from the incident light position on the surface of the living object, respectively;
an optical detector which detects light emitted from the luminescent material; and
a shield member which covers at least another surface of each of the one or more luminescent cells other than the first surface that is in contact with the surface of the living object, respectively, and which shields the luminescent material from stray light having the wavelength of the light from the one or more light irradiators, respectively, and a part of the shield member of each of the one or more luminescent cells transmits light emitted from the luminescent material, wherein the optical detector is disposed on the same side of the living object as the one or more light irradiators with respect to the surface of the living object on which each of the one or more luminescent cells is disposed, and wherein the optical detector measures a luminescence intensity of the light emitted from the luminescent material of each of the one or more luminescent cells, respectively, while the light is irradiated by the one or more light irradiators, respectively, and absorption information of the incident light in the living object is measured from the luminescence intensity measured by the optical detector.

2. The optical measurement apparatus according to claim 1, wherein the one or more luminescent cells have a triangular shape and the optical detector is an image-pickup device.

3. The optical measurement apparatus according to claim 1, wherein a marker is disposed at the incident light position, and the marker is irradiated with light by the one or more light irradiators from a position apart from the living object, and a mechanism of tracking the marker even when the living object moves is provided.

4. The optical measurement apparatus according to claim 1, further comprising:

a mechanism of correcting the detected luminescence intensity based on a positional relation between the optical detector or the light irradiators and the living object.

5. The optical measurement apparatus according to claim 1, wherein light emitted from the luminescent material has a wavelength different than the wavelength of light from the one or more light irradiators.

6. The optical measurement apparatus according to claim 1, wherein the shield member covers plural surfaces of each of the one or more luminescent cells other than the first surface that is in contact with the surface of the living object.

7. The optical measurement apparatus according to claim 1, wherein the shield member covers all surfaces of each of the one or more luminescent cells other than the first surface that is in contact with the surface of the living object.

* * * * *